United States Patent
Chou et al.

(10) Patent No.: US 10,716,484 B2
(45) Date of Patent: Jul. 21, 2020

(54) FIRST-AID DEVICE FOR DETECTING MYOCARDIAL INFARCTION

(71) Applicant: Wen-Pin Chou, Taipei (TW)

(72) Inventors: Wen-Pin Chou, Taipei (TW);
Hsun-Chieh Chiu, Taipei (TW);
Tsung-Min Lin, Taipei (TW);
Tsung-Hsing Chen, Taipei (TW);
Meng-Chu Chang, Taipei (TW)

(73) Assignee: Asiatic Fiber Corporation, Taoyuan (TW)

( * ) Notice: Subject to any disclaimer, the term of this patent is extended or adjusted under 35 U.S.C. 154(b) by 0 days.

(21) Appl. No.: 16/510,013

(22) Filed: Jul. 12, 2019

(65) Prior Publication Data

US 2020/0015698 A1    Jan. 16, 2020

(30) Foreign Application Priority Data

Jul. 14, 2018   (TW) .............................. 107122482 A

(51) Int. Cl.
| | |
|---|---|
| *A61B 5/0408* | (2006.01) |
| *G16H 50/30* | (2018.01) |
| *A61N 1/04* | (2006.01) |
| *A61B 5/00* | (2006.01) |
| *A61B 5/0452* | (2006.01) |
| *A61B 5/024* | (2006.01) |
| *A61B 5/04* | (2006.01) |
| *A61B 5/0205* | (2006.01) |

(52) U.S. Cl.
CPC ........ *A61B 5/04085* (2013.01); *A61B 5/6804* (2013.01); *A61B 5/746* (2013.01); *A61N 1/0484* (2013.01); *G16H 50/30* (2018.01); *A61B 5/0205* (2013.01); *A61B 5/02438* (2013.01); *A61B 5/04012* (2013.01); *A61B 5/0452* (2013.01); *A61B 5/6823* (2013.01)

(58) Field of Classification Search
CPC ... A61B 5/04085; A61B 5/6804; A61B 5/746; G16H 50/30; A61N 1/0484
USPC ...................................................... 340/539.12
See application file for complete search history.

(56) References Cited

U.S. PATENT DOCUMENTS

| | | | |
|---|---|---|---|
| 8,750,971 B2* | 6/2014 | Tran ..................... | A61B 5/0006 600/509 |
| 9,757,579 B2* | 9/2017 | Foshee, Jr. ........... | A61N 1/0484 |
| 2015/0278475 A1* | 10/2015 | Shor ...................... | G06Q 50/01 705/2 |
| 2017/0003356 A1* | 1/2017 | Kaib ..................... | A61N 1/3708 |

(Continued)

*Primary Examiner* — John A Tweel, Jr.
(74) *Attorney, Agent, or Firm* — Wang Law Firm, Inc.

(57) ABSTRACT

A first-aid device for detecting myocardial infarction, including a wearable textile, a first alarm detection unit, a second detection alarm unit, and a charging first-aid unit for actively detecting and alerting to myocardial infarction, instantly supplying crucial medicine, and providing a charging function. In particular, the wearable textile put on a patient carries the first alarm detection unit actively detecting myocardial infarction, the charging first-aid unit instantly provides the user medicine to alleviate painful symptom, and at the same time, the second detection alarm unit serves as a spare part while the first alarm detection unit is charged by the charging first-aid unit. As a result, the first alarm detection unit and the second detection alarm unit are alternatively used for actively and ceaselessly detecting myocardial infarction assuring first-aid for the patient.

4 Claims, 2 Drawing Sheets

(56) References Cited

U.S. PATENT DOCUMENTS

2019/0061772 A1* 2/2019 Prinz .................... B60W 40/08
2019/0298987 A1* 10/2019 Freeman .............. A61N 1/3904

* cited by examiner

FIRST-AID DEVICE FOR DETECTING MYOCARDIAL INFARCTION

CROSS-REFERENCE TO RELATED APPLICATION

This application claims the priority of Taiwanese patent application No. 107124482, filed on Jul. 14, 2017, which is incorporated herewith by reference.

BACKGROUND OF THE INVENTION

1. Field of the Invention

The present invention relates to a first-aid device, and more specifically to a first-aid device for detecting myocardial infarction employing a wearable textile placed on a user to carry a first alarm detection unit for actively detecting myocardial infarction, providing the user medicine to alleviate painful symptom through a charging first-aid unit connected to the first alarm detection unit, and charging a second detection alarm unit as a spare part through the first alarm detection unit.

2. Background

As is well known, most people prefer meat and greasy food with heavy salt, and lack vegetables and fruit, particularly without doing elementary exercise, and consequently, some lethal cardiovascular disease like arteriosclerosis, aortic dissection, cerebral stroke, or myocardial infarction possibly develops, even resulting in sudden death.

Generally, the patient once suffering from cardiovascular disease will lose 10% chance of survival for every one minute delay of first-aid. And, if first-aid is delayed over 5 minutes, serious damage of the body is permanent. Thus, it is crucial to render medical assistance as soon as possible.

As with myocardial infarction, the coronary artery supplying nutrients and oxygen to the heart may become narrow and retard blood flow because of smoking, high blood pressure, and high blood lipids. Once the coronary artery is blocked to cause the blood flowrate to reduce to a dangerous level, the patient will suffer from chest distress, chest pain, cold sweat, angina pectoris, or even myocardial infarction. In particular, acute and lethal myocardial infarction often happens when the environmental temperature quickly drops, or after the patient exercises intensely or immerses in a warm bath too long. At this time, if the patient takes one sublingual tablet like nitroglycerin, the blood vessel immediately expands to alleviate the level of myocardial infarction and avoid completely ceasing blood flow to the heart. Thus, the heart can temporarily function, and the patient acquires enough time for first-aid while being delivered to the hospital.

Commonly, the sublingual tablet takes effect after one to three minutes, and the patient should find relieve from myocardial infarction after five minutes at most. Therefore, the patient may take one sublingual tablet every five minutes before being delivered to the hospital, but a total of three sublingual tablets is the maximum. To assure the effect of the medicine, it is recommended to carry the sublingual tablets readily in a brown medicine bottle. However, it is not appropriate to put the sublingual tablets in the pocket closely attached to a patient's body because body temperature deteriorates the effect of the medicine.

From the above mentioned, the patient should first correctly judge and identify by himself or herself that myocardial infarction has occurred, and then immediately take the sublingual tablet from the medicine bottle and quickly keep it under the tongue in the mouth for gradually releasing. However, when the patient is fatigued from exercise, or suffers from headache or pain due to bad sleep, cold, dyspepsia, apepsia, or ulcer, judgment is possibly biased and myocardial infarction is not correctly identified, unfortunately losing the chance of taking the medicine for first-aid in time.

In addition, when the patient fails to take the medicine or clearly tell people the location of the medicine, no one can help the patient to relieve the symptoms, and the only recourse is to call the ambulance. Consequently, the patient may suffer from serious and permanent disability or even death.

Therefore, an urgent need exists to provide a first-aid device for detecting myocardial infarction employing a wearable textile put on a user to carry a first alarm detection unit for actively detecting myocardial infarction, providing the user medicine to alleviate painful symptom through a charging first-aid unit connected to the first alarm detection unit, and charging a second detection alarm unit as a spare part through the first alarm detection unit, thereby overcoming the problems in the prior arts.

SUMMARY OF THE INVENTION

The primary objective of the present invention is to provide a first-aid device for detecting myocardial infarction, generally comprising a wearable textile, a first alarm detection unit, a second detection alarm unit, and a charging first-aid unit for actively detecting and alarming myocardial infarction, instantly supplying crucial medicine, and providing a charging function.

Specifically, the wearable textile-like comfortable underwear is suitably put on a user or patient and provided with a plurality of sensing electrodes, a plurality of conductive connections, and a connection slot. The sensing electrodes are particularly configured to attach to the chest of the user such as around the heart for sensing and transmitting a physiological signal from the chest. The sensing electrodes are connected to the connection slot through the conductive connections.

The first alarm detection unit and the second alarm detection unit are implemented by the same electric design. However, the first alarm detection unit serves as an operating detection alarm unit, and the second alarm detection unit serves as a spare detection alarm unit for replacing the first alarm detection unit if needed. Further, the first alarm detection unit is configured to operate constantly and comprises a connection port for connecting the connection slot in a detachable manner. The first alarm detection unit receives the physiological signal, generates and transfers an emergency alarm signal based on the physiological signal, and processes an alarm operation such as a specific sound, vibration, or light signal. Also, the second alarm detection unit is provided with a connecting port, and configured to remain in a standby status.

The above charging first-aid unit comprises a charging space for accommodating and charging the second detection alarm unit, and a medicine box for accommodating at least one sublingual tablet. In addition, the charging space is provided with a charging slot.

Further, the emergency alarm signal is received by a remote processing unit for an operator of the remote processing unit to perform an emergency treatment.

Additionally, each of the first alarm detection unit and the second alarm detection unit comprises a charging port, a controller, an alarm, and a rechargeable battery. The rechargeable battery supplies power to the controller and the alarm for operation. The charging port of the second alarm detection unit is electrically connected to the charging slot of the charging space of the charging first-aid unit for charging in another detachable manner. The controller is electrically connected to the charging port and the alarm, receives the physiological signal, and determines if the user suffers from myocardial infarction based on the physiological signal. When the user suffers from myocardial infarction, the controller generates and transfers the emergency alarm signal, and the alarm receives the emergency alarm signal and performs an alarm operation based on the emergency alarm signal for informing and reminding the user to take the sublingual tablet from the medicine box.

Moreover, the charging first-aid unit further comprises a charge controller and a rechargeable battery module, and the charge controller is provided with a universal serial bus (USB) input port for connecting an external power source, and a power output port for connecting the charging slot. The charge controller is connected to the rechargeable battery module for charging the rechargeable battery module by an external power from the external power source through the USB input port, and the charge controller outputs an output power from the rechargeable battery module to the charging slot through the power output port.

Therefore, the present invention can actively detect that the user suffers from myocardial infarction so as to avoid erroneous judgment and losing precious time for first-aid, and the user can easily carry and readily employ the charging first-aid unit to provide crucial medicine to alleviate painful symptom so as to prolong the critical window for a medical intervention. In addition, a specific sound, vibration, or light signal is employed to remind people around the user of taking the medicine from the charging first-aid unit for the user to take, thereby greatly increasing the chance of survival. Moreover, the charging first-aid unit charges the second alarm detection unit, and when the first alarm detection unit is removed, the second alarm detection unit is ready to replace the first alarm detection unit. As a result, the ceaseless active detection is maintained, and the user suffering from myocardial infarction is assured the chance of first-aid.

BRIEF DESCRIPTION OF THE DRAWINGS

The present invention will be apparent to those skilled in the art by reading the following detailed description of a preferred embodiment thereof, with reference to the attached drawings, in which.

DETAILED DESCRIPTION OF THE PREFERRED EMBODIMENT

The accompanying drawings are included to provide a further understanding of the invention, and are incorporated in and constitute a part of this specification. The drawings illustrate embodiments of the invention and, together with the description, serve to explain the principles of the invention.

Figure 1:
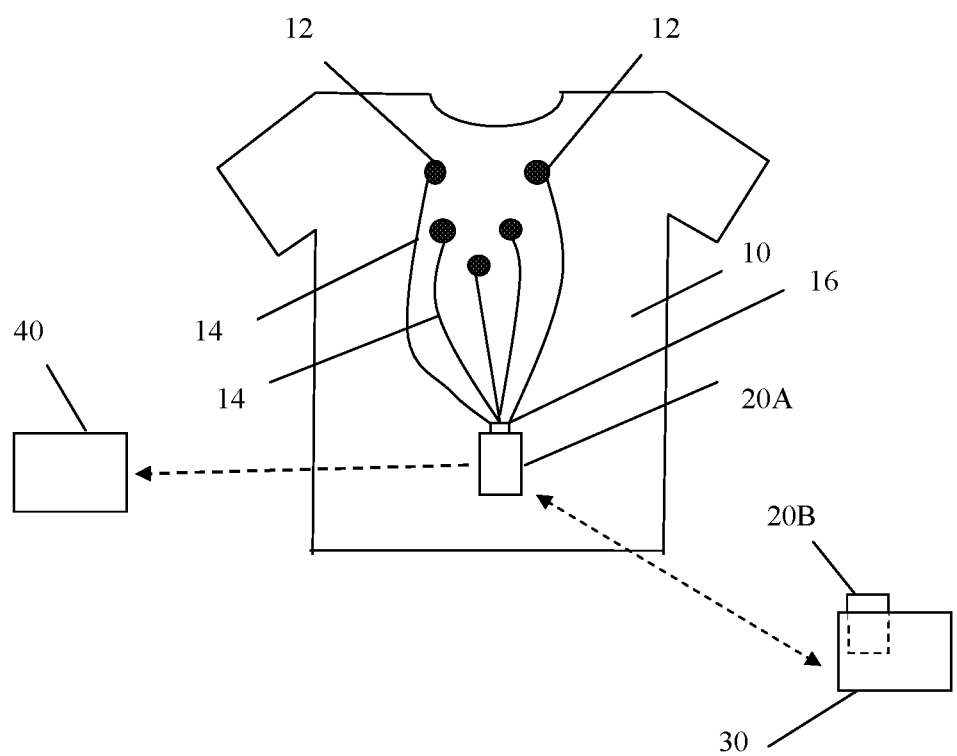
FIG. 1 shows the first-aid device for detecting myocardial infarction according to the embodiment of the present invention.

Please refer to FIG. 1, showing the first-aid device for detecting myocardial infarction according to the embodiment of the present invention. As shown in FIG. 1, the first-aid device for detecting myocardial infarction of the present invention generally comprises a wearable textile 10, a first alarm detection unit 20A, a second detection alarm unit 20B, and a charging first-aid unit 30 for actively detecting and alarming myocardial infarction, instantly supplying crucial medicine, and providing a function of charging so as to prevent the patient suffering from myocardial infarction from sudden death due to lack of medical treatment, and further acquiring precious time for subsequent treatment.

Specifically, the wearable textile 10 is put on a user or patient, and the first alarm detection unit 20A is provided on the wearable textile 10, the first alarm detection unit 20A serves as an operating detection alarm unit, and [[keeps]] is in an operation status. Additionally, the second detection alarm unit 20B serves as a spare detection alarm unit, remains in a standby status, and is accommodated in and charged by the charging first-aid unit 30.

The wearable textile 10 is provided with a plurality of sensing electrodes 12, a plurality of conductive connections 14, and a connection slot 16. Each of the conductive connections 14 is connected to the corresponding sensing electrode 12 and the connection slot 16, and the sensing electrodes 12 are preferably provided on the chest of the user like the place around the heart for sensing and transferring a physiological signal like Electrocardiogram (ECG) to the connection slot 16 through the conductive connections 14. In general, the present invention needs at least five sensing electrodes 12 to acquire the physiological signal with sufficient precision.

Further, the sensing electrodes 12, the conductive connections 14, and the connection slot 16 are specifically provided on the inside of the wearable textile 10 such that the sensing electrodes 12 are well attached onto the body of the user after the user puts on the wearable textile 10 to easily sense the physiological signal, and the sensing electrodes 12, the conductive connections 14, and the connection slot 16 are not exposed outside so that an aesthetic appearance is maintained. In addition, the connection slot 16 can be designed to be exposed outside for the user to easily and readily remove or insert the first alarm detection unit 20A.

The first alarm detection unit 20A and the second alarm detection unit 20B are implemented with the same electric function, and one difference between the first alarm detection unit 20A and the second alarm detection unit 20B is that the first alarm detection unit 20A has sufficient power and is connected to the connection slot 16 of the wearable textile 10 for normal operation, and the second alarm detection unit 20B is insufficient in power and charged by the charging first-aid unit 30. Thus, only the first alarm detection unit 20A is explained in detail for technical aspects in the following description.

Figure 2:
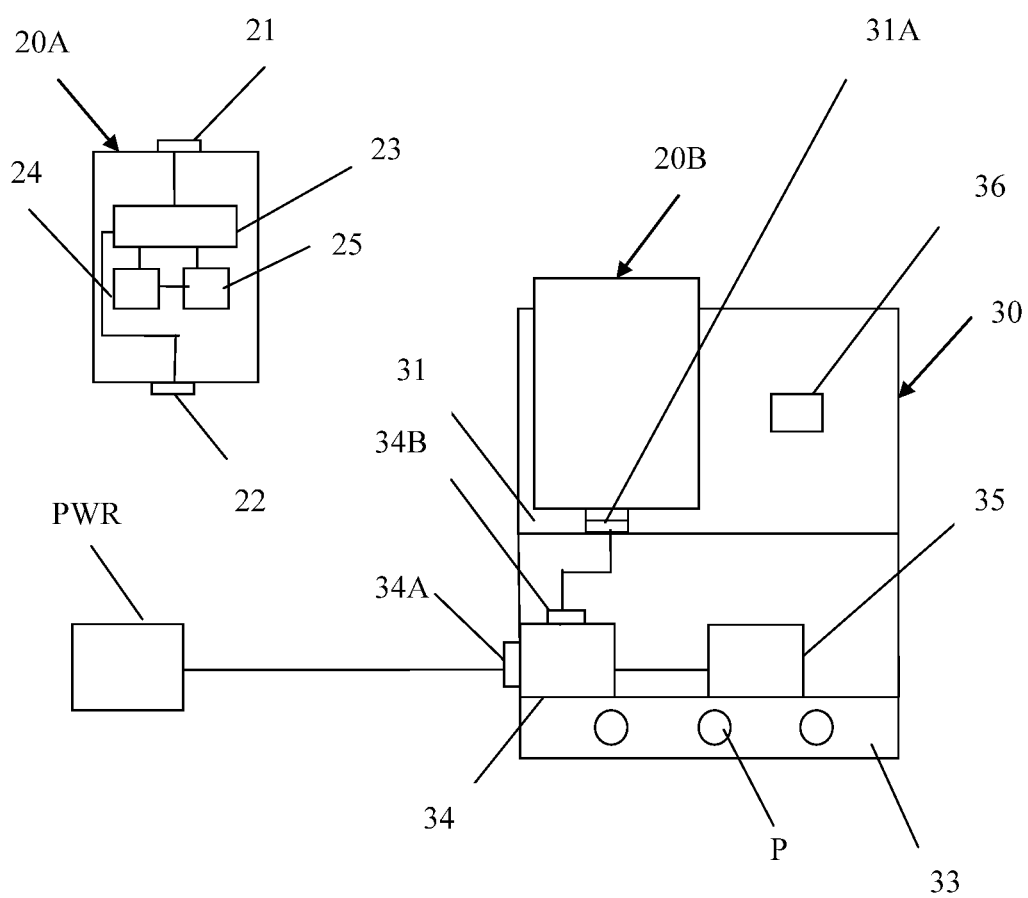
FIG. 2 shows the first alarm detection unit of the first-aid device according to the embodiment of the present invention.

In FIG. 2, the first alarm detection unit 20A comprises a connection port 21 for connecting the connection slot 16 in a detachable manner to receive the physiological signal, generate and transfer an emergency alarm signal based on the physiological signal, and at the same time, perform an alarm operation. Moreover, the first alarm detection unit 20A comprises a charging port 22, a controller 23, an alarm 24, and a rechargeable battery 25. The rechargeable battery 25 supplies power to the controller 23 and the alarm 24 for operation. The controller 23 is electrically connected to the charging port 22 and the alarm 24, receives the physiological signal, and determines if the user suffers from myocardial infarction based on the physiological signal. The controller 23 generates and transfers the emergency alarm signal when the user suffers from myocardial infarction. The alarm 24 receives the emergency alarm signal and performs the alarm operation based on the emergency alarm signal. In addition, the emergency alarm signal is received by a remote processing unit 40 for an operator of the remote processing unit 40 to perform an emergency treatment so as to assist the user suffering from myocardial infarction. For instance, the first alarm detection unit 20A transmits the emergency alarm signal through a 5G wireless communication channel, and the emergency treatment of the remote processing unit 40 comprises calling an ambulance or at least one medical personnel to the location of the user for performing first-aid.

Furthermore, the first alarm detection unit 20A stores and transfers the physiological signal to the remote processing unit 40 for detailed examination and analysis.

Each of the first alarm detection unit 20A and the second alarm detection unit 20B comprises a battery status indicating light (not shown) to indicate that the rechargeable battery 25 is in a charging status, a charging complete status, or a power insufficiency status. Specifically, the battery status indicating light is intended to inform or remind the user that the first alarm detection unit 20A is insufficient in power and to remove the first alarm detection unit 20A from the connection port 16 of the wearable textile 10 and further place the first alarm detection unit 20A in the charging first-aid unit 30 for charging. When the first alarm detection unit 20A is in charging complete status, the first alarm detection unit 20A is inserted into the connection port 16 of the wearable textile 10 for normal use.

Preferably, the user can easily and readily carry the charging first-aid unit 30 for use. More specifically, the charging first-aid unit 30 comprises a charging space 31 and a medicine box 33, and the charging space 31 comprises a charging slot 31A. The second detection alarm unit 20B is accommodated in the charging space 31 for charging, and the medicine box 33 accommodates at least one sublingual tablet P like a nitroglycerin sublingual tablet for urgently expanding the blood vessels and lasting for 30 minutes.

One primary function provided by the above alarm 24 is to employ the alarm operation to alarm or remind the user of instantly opening the medicine box 33 and taking the sublingual tablet P. The alarm operation comprises generating a specific sound, vibration, or light signal. For instance, the sound comprises a piece of voice like "myocardial infarction, please take the sublingual tablet right now", which also informs or reminds some people around the user to open the medicine box 33 and take the sublingual tablet P for the user, thereby acquiring some precious time for first-aid and preventing the heart from sudden cardiac arrest or permanent damage due to insufficient blood supply.

Further, in another detachable manner, the charging port 22 of the second alarm detection unit 20B is electrically connected to the charging slot 31A of the charging space 31 of the charging first-aid unit 30 for charging.

More specifically, the charging first-aid unit 30 comprises a charge controller 34 and a rechargeable battery module 35. The charge controller 34 is provided with a universal serial bus (USB) input port 34A for connecting an external power source PWR, and a power output port 34B for connecting the charging slot 31A. The charge controller 34 is connected to the rechargeable battery module 35 for charging the rechargeable battery module 35 by an external power from the external power source PWR through the USB input port 34A, and the charge controller 34 outputs an output power from the rechargeable battery module 35 to the charging slot 31A through the power output port 34B.

Moreover, the charging first-aid unit 30 further comprises a wireless communication unit 36 for linking to the first alarm detection unit 20A in a wireless manner like blue tooth, Zigbee or WiFi to sustain a communication operation. The first alarm detection unit 20A employs the communication operation to determine if a distance between the first alarm detection unit 20A and the charging first-aid unit 30 is larger than an upper threshold. If the distance is larger than the upper threshold, the first alarm detection unit 20A generates an alarm sound, an alarm vibration, or an alarm light signal to instantly inform of the user that the charging first-aid unit 30 is not within the preset safety range. It is possible the charging first-aid unit 30 is carelessly left behind, and it is necessary to bring it back, otherwise the user loses the chance of taking the sublingual tablet P for first-aid once suffering from myocardial infarction.

From the above mentioned, one feature of the present invention is that the wearable textile is put on a user and carries the first alarm detection unit for actively and ceaselessly detecting myocardial infarction to avoid erroneous judgment and losing precious time for first-aid, and the user easily carries and readily employs the charging first-aid unit to provide crucial medicine to alleviate painful symptom so as to prolong the first-aid time and increase the chance of receiving medical aid.

In particular, when the user suffers from myocardial infarction, loses consciousness, or does not speak clearly to ask people for help, the first alarm detection unit actively generates sound, vibration, or light signal to inform nearby people of taking of the medicine from the charging first-aid unit for the user to take, thereby greatly increasing the chance of survival.

Another feature of the present invention is that the charging first-aid unit provides the function of charging and accommodating the second alarm detection unit as a spare part. Thus, when the first alarm detection unit is insufficient in power, the first alarm detection unit is readily taken off and instantly replaced by the second alarm detection unit. Then, the charging first-aid unit charges the first alarm detection unit. In this manner the patient may be continuously monitored. In other words, the first alarm detection unit and the second alarm detection unit are alternatively employed to assure the user suffering from myocardial infarction of acquiring the chance of first aid.

Although the present invention has been described with reference to the preferred embodiments thereof, it is apparent to those skilled in the art that a variety of modifications and changes may be made without departing from the scope of the present invention which is intended to be defined by the appended claims.

What is claimed is:

1. A first-aid device for detecting myocardial infarction, comprising:

a wearable textile put on a user and provided with a plurality of sensing electrodes, a plurality of conductive connections, and a connection slot, the sensing electrodes attached onto a chest of the user for sensing and transmitting a physiological signal from the chest, the sensing electrodes connected to the connection slot through the conductive connections;

a first detection alarm unit serving as an operating detection alarm unit and comprising a connection port for connecting the connection slot in a detachable manner, the first detection alarm unit receiving the physiological signal, generating and transferring an emergency alarm signal based on the physiological signal, and processing an alarm operation;

a second detection alarm unit serving as a spare detection alarm unit, comprising a connection port, and remaining in a standby status for replacing the first detection alarm unit; and a charging first-aid unit comprising a charging space for accommodating and charging the second detection alarm unit, and a medicine box for accommodating at least one sublingual tablet, the charging space provided with a charging slot, wherein the alarm operation comprises generating a sound, vibration, or a light signal, the emergency alarm signal is received by a remote processing unit for an operator of the remote processing unit to perform an emergency treatment, each of the first detection alarm unit and the second detection alarm unit comprises a charging port, a controller, an alarm, and a rechargeable battery, the rechargeable battery supplies power to the controller and the alarm for operation, the charging port of the second detection alarm unit is electrically connected to the charging slot of the charging space of the charging first-aid unit for charging in an another detachable manner, the controller is electrically connected to the charging port and the alarm, receives the physiological signal, and determines if the user suffers from myocardial infarction based on the physiological signal, the controller generates and transfers the emergency alarm signal when the user suffers from myocardial infarction, the alarm receives the emergency alarm signal and performs an alarm operation based on the emergency alarm signal for informing and reminding the user of taking the sublingual tablet from the medicine box, the charging first-aid unit further comprises a charge controller and a rechargeable battery module, the charge controller is provided with a universal serial bus (USB) input port for connecting an external power source, and a power output port for connecting the charging slot, the charge controller is connected to the rechargeable battery module for charging the rechargeable battery module by an external power from the external power source through the USB input port, and the charge controller outputs an output power from the rechargeable battery module to the charging slot through the power output port.

2. The first-aid device as claimed in claim 1, wherein the first detection alarm unit transmits the emergency alarm signal through a 5G wireless communication channel, and the emergency treatment comprises calling an ambulance or at least one medical personnel of arriving on a location of the user.

3. The first-aid device as claimed in claim 1, wherein the charging first-aid unit further comprises a wireless communication unit for linking the first detection alarm unit in a wireless manner to sustain a communication operation, the first detection alarm unit employs the communication operation to determine if a distance between the first detection alarm unit and the charging first-aid unit is larger than an upper threshold, and the first detection alarm unit generates an alarm sound, an alarm vibration, or an alarm light signal when the distance is larger than the upper threshold.

4. The first-aid device as claimed in claim 3, wherein the wireless manner comprises blue tooth, Zigbee or WiFi.

* * * * *